(12) United States Patent
Forte

(10) Patent No.: US 11,197,659 B2
(45) Date of Patent: Dec. 14, 2021

(54) URINE COLLECTION DEVICE

(71) Applicant: FORTE MEDICAL LIMITED, London (GB)

(72) Inventor: Giovanna F. L. Forte, London (GB)

(73) Assignee: FORTE MEDICAL LIMITED, London (GB)

( * ) Notice: Subject to any disclaimer, the term of this patent is extended or adjusted under 35 U.S.C. 154(b) by 1175 days.

(21) Appl. No.: 14/772,451

(22) PCT Filed: Mar. 4, 2014

(86) PCT No.: PCT/GB2014/050630
§ 371 (c)(1),
(2) Date: Sep. 3, 2015

(87) PCT Pub. No.: WO2014/135856
PCT Pub. Date: Sep. 12, 2014

(65) Prior Publication Data
US 2016/0022249 A1    Jan. 28, 2016

(30) Foreign Application Priority Data

Mar. 4, 2013    (GB) ...................................... 1303799

(51) Int. Cl.
*A61B 10/00*          (2006.01)
(52) U.S. Cl.
CPC .................................. *A61B 10/007* (2013.01)
(58) Field of Classification Search
CPC .................................................... A61B 10/007
See application file for complete search history.

(56) References Cited

U.S. PATENT DOCUMENTS

| | | | | |
|---|---|---|---|---|
| 2,850,050 A | * | 9/1958 | Connolly ............. | A61B 10/007 141/126 |
| 3,161,891 A | * | 12/1964 | Bauman ............... | A61B 10/007 600/574 |
| 3,177,500 A | * | 4/1965 | Bauman ............... | A61B 10/007 4/144.3 |

(Continued)

FOREIGN PATENT DOCUMENTS

| | | |
|---|---|---|
| CA | 2170936 | 9/1996 |
| EP | 2140903 | 1/2010 |

(Continued)

*Primary Examiner* — Rene T Towa
(74) *Attorney, Agent, or Firm* — Hahn Loeser + Parks LLP; Scott M. Oldham

(57) ABSTRACT

A urine collection device 1 comprises a collector 2 to collect urine voided by a user, first and second outlets 3, 4 to allow urine to drain from the device, the first outlet 3 being adapted for connection to a receptacle 5 for a urine sample, and the second outlet 4 comprising an overflow outlet. A diverter device 6 is provided having first and second operative states, such that in a first state the diverter device 6 allows urine to flow through the first outlet 3 to the receptacle 5 for collection of a forestream sample, and in a second state the diverter device 6 prevents flow to the first outlet 3 and allows flow to the overflow outlet, the diverter device 6 being unable to return from the second state to the first state. The collector 2 is preferably a funnel 7 whose open lower end 11 forms one of the outlets, and also has the other outlet in the funnel wall.

11 Claims, 4 Drawing Sheets

(56) References Cited

U.S. PATENT DOCUMENTS

| | | | |
|---|---|---|---|
| 3,750,648 A * | 8/1973 | Gleason | A61B 10/007 4/144.3 |
| 3,943,770 A * | 3/1976 | McDonald | A61B 10/007 73/863.52 |
| 3,982,898 A | 9/1976 | McDonald | |
| 4,106,490 A | 8/1978 | Spilman et al. | |
| 4,230,808 A * | 10/1980 | Pietersen | A62D 1/0021 428/321.5 |
| 4,276,889 A * | 7/1981 | Kuntz | G01N 1/10 4/144.1 |
| 4,331,162 A * | 5/1982 | Kuntz | G01N 1/10 600/574 |
| 4,492,258 A | 1/1985 | Lichtenstein et al. | |
| 4,494,581 A * | 1/1985 | Gordon | A61B 10/007 141/1 |
| 4,769,215 A | 9/1988 | Ehrenkranz | |
| 4,891,993 A | 1/1990 | Barker | |
| 5,105,824 A | 4/1992 | Rasch | |
| 5,711,310 A | 1/1998 | Vinayagamoorthy et al. | |
| 5,766,136 A * | 6/1998 | Cawood | A61B 10/007 600/573 |
| 7,172,559 B2 | 2/2007 | Yong et al. | |
| 7,435,242 B2 | 10/2008 | Levinson | |
| 7,547,298 B2 | 6/2009 | Lee et al. | |
| 7,871,385 B2 | 1/2011 | Levinson | |
| 2002/0042145 A1 | 4/2002 | Forsberg | |
| 2003/0149408 A1 | 8/2003 | Levinson | |
| 2006/0064034 A1 | 3/2006 | Stewart et al. | |
| 2008/0228106 A1 * | 9/2008 | Forte | A61F 5/4556 600/575 |
| 2011/0040272 A1 | 2/2011 | Forte et al. | |
| 2011/0237977 A1 * | 9/2011 | Knight | A61B 10/007 600/573 |
| 2011/0238977 A1 | 9/2011 | Talbert et al. | |

FOREIGN PATENT DOCUMENTS

| | | |
|---|---|---|
| GB | 2247626 | 3/1992 |
| WO | 8603394 | 6/1986 |
| WO | 9013280 | 11/1990 |
| WO | 2005003725 | 1/2005 |
| WO | 2005107602 | 11/2005 |

* cited by examiner

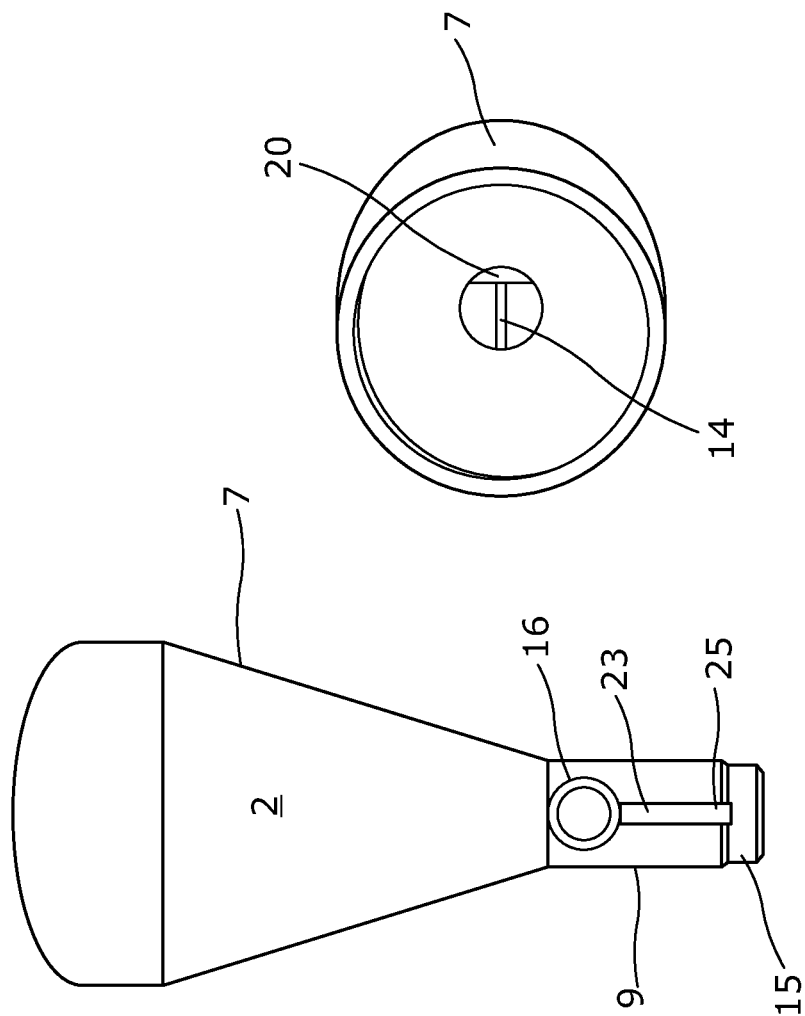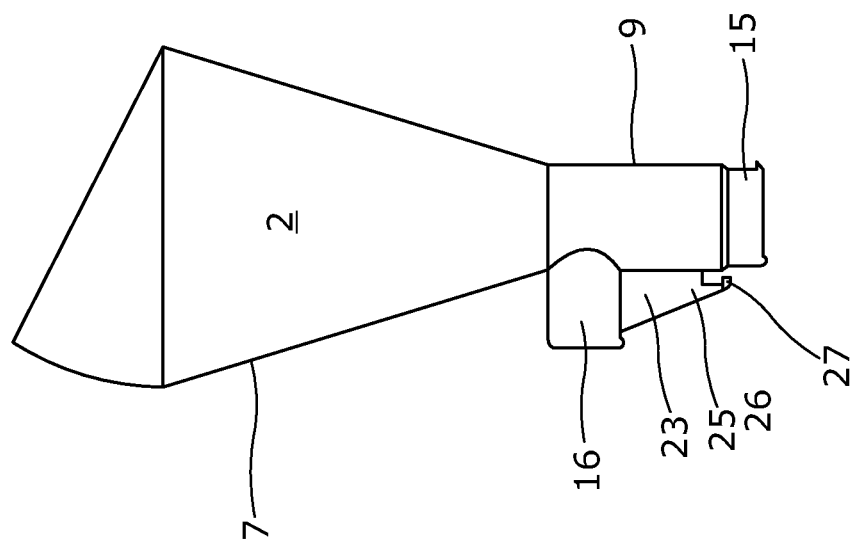

URINE COLLECTION DEVICE

CROSS REFERENCE TO RELATED APPLICATION

This is a U.S. national stage application of PCT/GB2014/050630 filed Mar. 4, 2013, to which this application claims priority from, the entire disclosure of which is hereby incorporated herein by reference in its entirety.

This invention relates to a device to assist in the collection of urine from a patient. In particular, the device is designed to collect initial urine flow, known as a forestream sample.

Analysis of urine is used as a diagnostic tool for detecting a wide range of conditions and disease. The urine can be analysed for particular chemicals that are indicative of infections or whose levels may indicate diseases, including cancer. Different conditions or diseases are detected by analysis of different parts of urine flow. The initial flow or forestream may have a higher concentration of bacteria or substances largely resident in the urethra, than the midstream flow. These might include infective organisms of urethritis such as gonococcus or chlamydia, or prostatic secretions. The forestream will not be as representative of the general composition of the urine, for example in detecting overall urinary protein or sugar levels, or general urinary tract infections. For these a midstream sample is preferred.

The patient is typically required to provide a urine sample in a sample bottle. Standard sample bottles are relatively small and have a narrow neck, making it difficult for the patient to deliver a sample accurately into the bottle. The part of the flow that is not required must also be disposed of, and it can be difficult to do this cleanly, especially for female patients.

Devices are known for assisting collection of a forestream sample. U.S. Pat. No. 7,547,298 shows a device having a funnel for collecting urine, an outlet connected through a valve to a sample bottle, and an overflow outlet. Initial flow is directed through the valve into the bottle, from which air leaves through a vent tube. When the urine level reaches the vent, no further flow into the bottle is possible, and the level of urine in the device rises to allow further flow to pass out through the overflow outlet. On completion of urination, the valve provides a further path to the overflow outlet to release a trapped volume. Another small volume is released into the bottle as it is detached. This device is efficient at capturing the forestream, but it has a complex construction, due to the valve.

A simpler construction is shown in WO 2005/107602. This has a funnel with a tube at its base leading to two outlets. A sample bottle is attached to the first outlet, while the second is an overflow outlet. A flow barrier is placed in the tube at the first outlet, to guide the initial flow preferentially to the bottle, and to allow air to leave the bottle. Once the bottle is full the urine passes to the overflow outlet. A valve may seal the forestream sample in the bottle. However, on removal of the bottle a trapped volume of urine in the first outlet will be released, which will be messy. The flow barrier provides a simple construction but its correct operation depends on the flow rate, and it cannot consistently ensure only or all of the forestream is guided to the bottle.

According to the present invention, we provide a urine collection device comprising a collector to collect urine voided by a user, first and second outlets to allow urine to drain from the device, the first outlet being adapted for connection to a receptacle for a urine sample, and the second outlet comprising an overflow outlet, and a diverter device having first and second operative states, such that in a first state the diverter device allows urine to flow through the first outlet to the receptacle for collection of a forestream sample, and in a second state the diverter device prevents flow to the first outlet and allows flow to the overflow outlet, the diverter device being unable to return from the second state to the first state.

Providing the diverter device with two operative states means that it will ensure efficient operation, both of collection of the forestream sample and the diversion of the remaining flow to the overflow outlet. As the diverter device does not return from the second state to the first it does not need to be a valve, and can thus have a simple construction, making the device overall of simple construction.

The device is designed to be used in a substantially vertical position, and so will be described in that orientation with the terms top, base, upper and lower referring to a vertical orientation.

Conveniently the collector comprises a funnel member, wider at the top for ease of use, and narrower at the base. The funnel member has a funnel wall comprising a substantially frusto-conical top portion, and a base portion. The lower end of the base portion is open. The base portion may be substantially cylindrical. One of the first and second outlets is provided by the open end of the base portion, and the other is provided in the funnel wall. The device preferably has only two outlets.

In one embodiment the first outlet is provided in the base portion of the funnel member, and the second, overflow outlet is provided in the funnel wall. The diverter device comprises a plug accommodated in the base portion, the plug in the first state allowing flow to the first outlet, and expanding on contact with liquid into the second state to prevent further flow to the first outlet and allow flow to the overflow outlet. The plug provides a particularly simple and effective construction of diverter device.

The base portion of the funnel member is adapted for connection of the receptacle, so that this is substantially vertical in use. Where the receptacle is a standard sample bottle the base portion may have means for engaging the external screw thread found at the top of the bottle, designed for attachment of the bottle cap.

The plug is preferably of an expandable sponge material. It is accommodated in the base portion of the funnel member. In this embodiment the base portion is substantially cylindrical. The plug may be an interference fit in the cylindrical base portion. The plug is located at its upper end by an abutment in the cylindrical base portion, and at its lower end projects from the cylindrical base portion. The lower end thus projects into the receptacle when this is attached to the device, and leaves a free space at the top of the receptacle when it is removed, to reduce the risk of spillage.

The second outlet comprises a tube extending from the funnel member substantially at right angles to the cylindrical base portion. The lowest part of the second outlet at its junction with the funnel wall is substantially level with the upper end of the plug, to ensure that all the flow which is not collected in the receptacle drains readily from the device. The inner end of the tube is angled so that at its highest part it projects into the funnel to substantially prevent flow through the second outlet while the plug is in the first state allowing flow to the first outlet. The outer end of the tube is shaped to direct the flow away from the receptacle. This helps to ensure that the outside of the receptacle is kept clean and dry.

In another embodiment the first outlet is provided in the funnel wall and the second, overflow outlet is provided by the open end of the base portion of the funnel member.

The base portion is again substantially cylindrical. The diverter device comprises a membrane located at the entrance to the second outlet, the membrane in the first state blocking the entrance to the second outlet and directing the flow to the first outlet, and breaking after contact with liquid to allow flow to the overflow outlet. This also provides a simple and effective construction of the diverter device.

The membrane is of any suitable material, such as paper sheet or plastic film, and is attached to the device by adhesive, for example.

The first outlet comprises a tube extending from the funnel member at an angle. The outer end of the tube is adapted for connection of the receptacle. The angle of the tube is chosen so that the receptacle is not horizontal. This ensures that there is free space at the top of the receptacle when it is removed, thus reducing the risk of spillage. The second outlet is at the lower open end of the base portion, which may be approximately vertical, or angled the same way as the first outlet.

In either embodiment the device is conveniently made of plastics material. It has a simple construction, and is easy to use, while collecting a forestream sample in an efficient manner.

Embodiments of the invention are illustrated, by way of example only, in the accompanying drawings, in which:

FIG. 2 is a side view of the device of FIG. 1;

FIG. 3 is a front view of the device of FIG. 1;

FIG. 4 is a top view of the device of FIG. 1;

Figure 1:
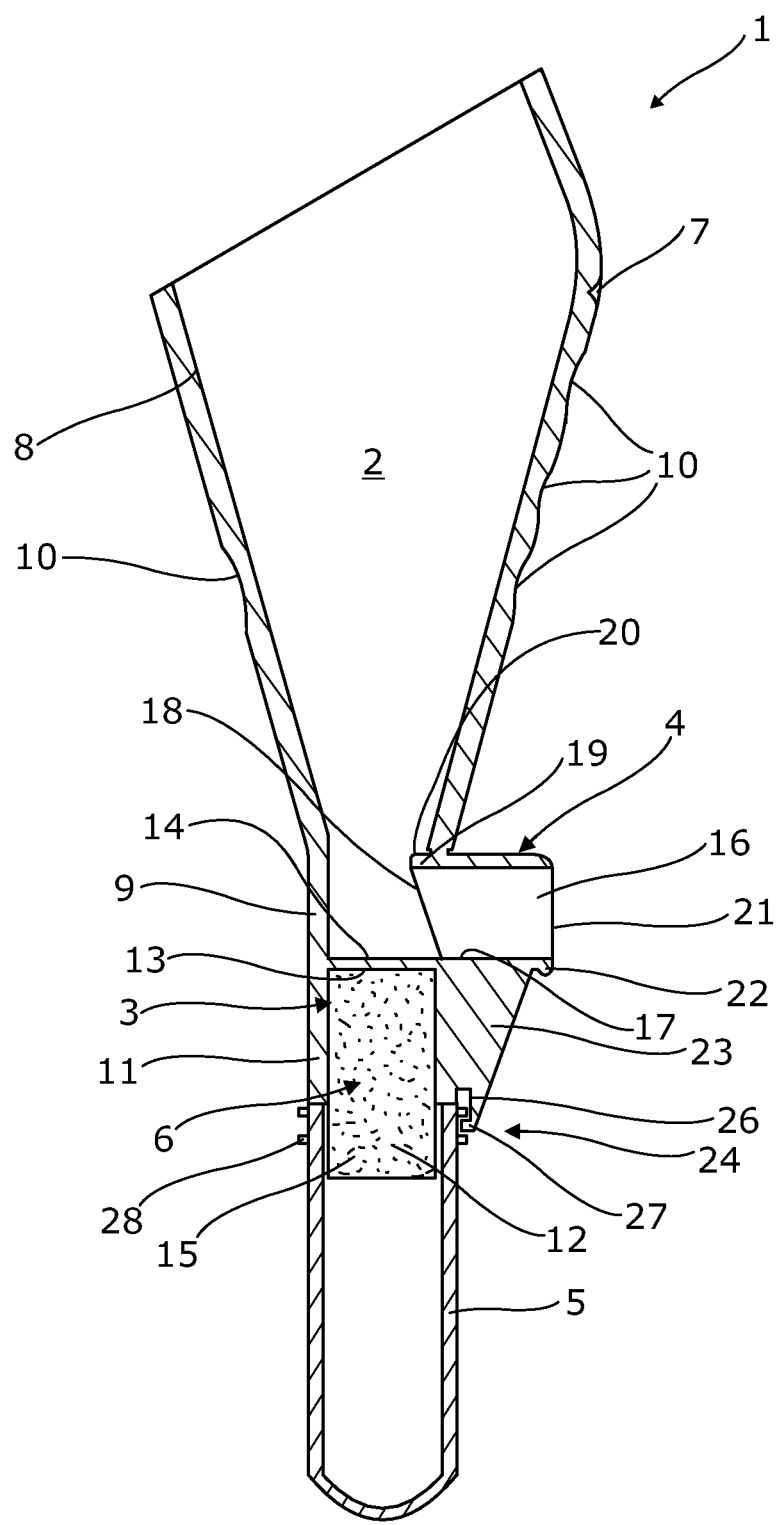
FIG. 1 is a longitudinal section through a urine collection device.
Figure 5:
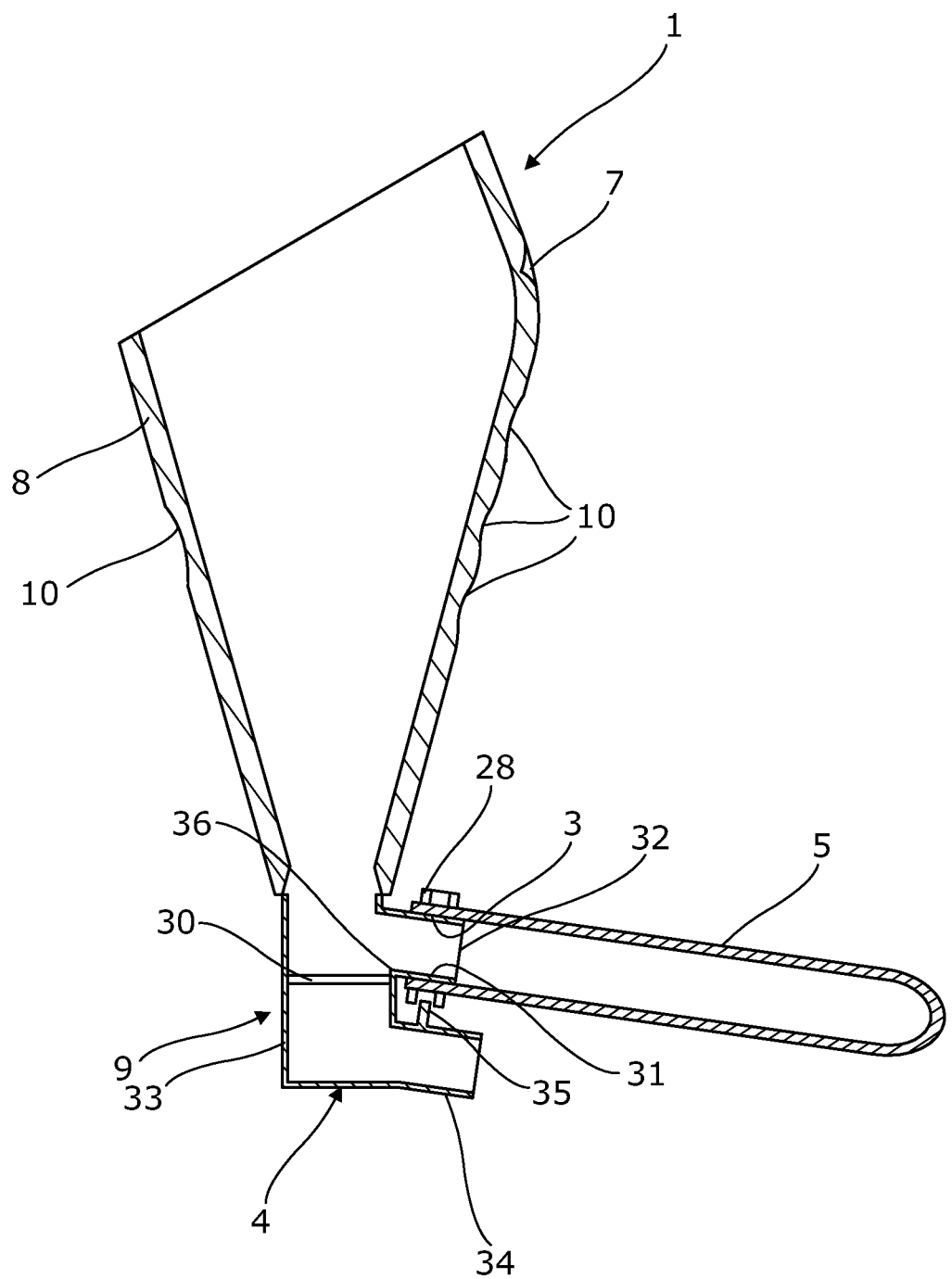
FIG. 5 is a longitudinal section through a modified urine collection device.
Figure 8:
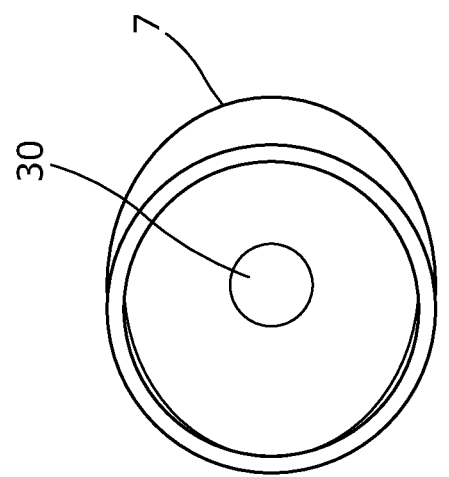
FIGS. 6 to 8 are similar to FIGS. 2 to 4, but showing the modified device of FIG. 5.
Figure 7:
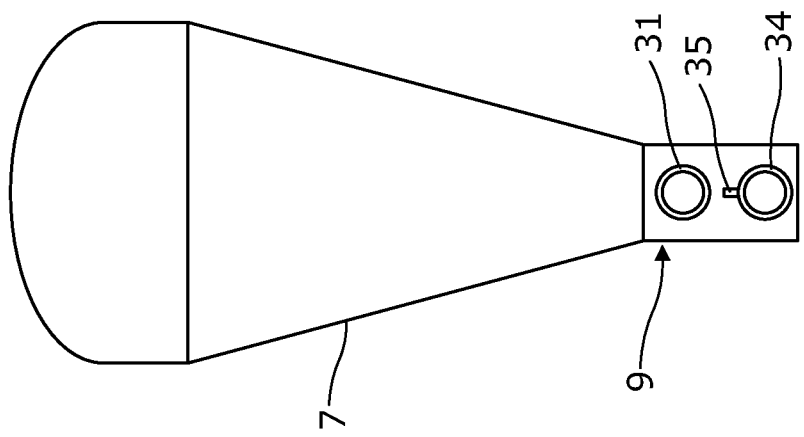
Figure 6:
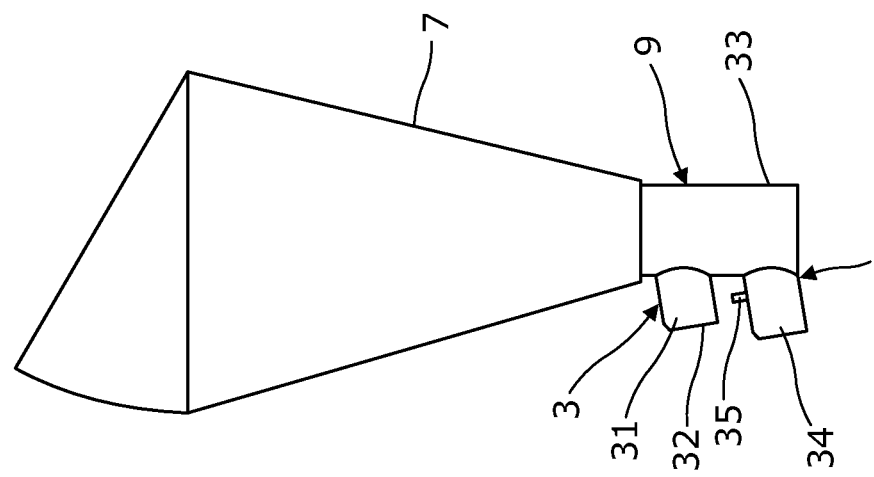

The urine collection device 1 shown in FIGS. 1 to 4 is for collection of a forestream sample of urine. The device 1 comprises a collector 2 to collect urine voided by a user, and first and second outlets 3, 4 respectively. The first outlet 3 is adapted for connection of a receptacle 5 for collection of the sample, and the second outlet 4 is an overflow outlet to deal with the urine flow following the forestream. A diverter device 6 is provided to direct the urine flow as required. The diverter device 6 has first and second operative states. In a first state the diverter device 6 allows urine to flow through the first outlet 3 to the receptacle 5 for collection of the forestream sample, and in a second state the diverter device 6 prevents flow to the first outlet 3 and allows flow to the second overflow outlet 4. The diverter device 6 cannot return to the first state from the second state.

The device 1 will be described in the vertical orientation shown, as it is the normal position of use. Terms such as top, base, upper and lower should be construed accordingly.

The collector 2 comprises a funnel member 7 having a wall with a wider top portion 8 of substantially frusto-conical shape, narrowing to a substantially cylindrical base portion 9. The top 8 is angled and shaped for ease of use. The outer surface has indentations 10 to indicate to the user how the device 1 is to be held. There is a single indentation 10 at the rear of the device 1 for the thumb, and three at the front for the fingers.

The first and second outlets 3, 4 are provided in the base portion 9 which has an open lower end 11. The first outlet is at the lower end 11 of the base portion 9. The receptacle 5 is connected to the lower end 11 so that it is vertical in use. The receptacle 5 is a standard sample bottle, and the manner of connection will be described below.

The diverter device 6 comprises an expandable plug 12 of sponge material. The plug 12 is substantially cylindrical and is an interference fit in the base portion 9. The sponge material is chosen so that in its first, dry state it allows urine to pass through it. The material expands on contact with liquid and so gradually moves into its second state, in which it prevents further urine flow through it. It will be appreciated that the plug cannot return from the second state to the first state. The position of the plug 12 in the base portion 9 is defined by abutment of its top surface 13 with a rail 14 (best seen in FIG. 4) which extends transversely across the base portion 9. The lower end 15 of the plug 12 projects below the lower end 11 of the base portion 9 and into the receptacle 5.

The second outlet 4 comprises a tube 16 extending substantially at right angles to the base portion 9, so approximately horizontally in use. The tube 16 projects from the funnel wall above the first outlet 3. As shown best in FIG. 1, the lowest point 17 of the tube 16 at its junction with the funnel wall is level with the top of the rail 14, so that it is just above the top surface 13 of the plug 12. This assists in ensuring that urine drains easily and fully from the device 1, as there will be no trapped volume of urine on completion of urination.

The inner end 18 of the tube 16 is angled, so that its top surface 19 projects slightly into the funnel member 7. This forms a guide surface 20 directing urine flow from the top of the funnel member 7 away from the overflow outlet 4. The outer end 21 of the tube 16 projects from the funnel member 7 so that urine leaving the device 1 through the overflow outlet 4 is directed away from the receptacle 5. The outer edge 22 is also shaped with a lip to ensure that the overflow urine leaves in a stream rather than dribbling back towards the funnel member 7.

The base portion 9 is formed with a lug 23 extending downwardly from the lowest point 17 of the tube 16 to project slightly beyond the lower end 11 of the base portion 9. It is best seen in FIGS. 1 and 3. The lug 23 provides rigidity for the device 1, and also the connection means 24 for the receptacle 5. At its lower end 25 the lug 23 has an upwardly-extending rebate 26 and an inwardly-extending projection 27, with which an external screw thread 28 on the receptacle 5 engages to attach the receptacle 5 to the device 1. The upper end 29 of the receptacle 5 engages the lower end 11 of the base portion 9.

The device is preferably injection-moulded in a suitable plastics material. It is simple to assemble, as the plug 12 is put in position in the base portion 9. The assembled device 1 (without the receptacle 5) will be packed in suitable protective packaging (not shown) to prevent contamination.

For use, the device 1 is removed from its packaging. A sterilised sample bottle has its top (not shown) removed, and the bottle is then screwed onto the base portion 9 to act as the receptacle 5. The user then urinates into the top portion 8 of the funnel member 7. The guide surface 20 ensures that the initial urine flow passes to the first outlet 3, through the plug 12 (which is in its first state) and into the receptacle 5. The plug 12 expands on contact with the urine and assumes its second state, in which further flow through the first outlet 3 is prevented. Urine flow is then directed to the second outlet 4 until urination is completed. The urine drains fully from the device 1 through the second outlet 4. The receptacle 5 can then be unscrewed, leaving the plug 12 in the device 1, so that there is a free space at the top of the receptacle 5.

This reduces the risk of spillage on removal of the receptacle 5. The receptacle 5 containing the forestream sample can then be recapped.

The forestream sample is taken efficiently, with very little or no mess, as the overflow outlet 4 directs the unwanted urine away from the receptacle 5. The only urine remaining in the device 1 is in the plug 12, whose material is chosen so that it does not drip.

FIGS. 5 to 8 show a modification of the urine collection device of FIGS. 1 to 4, and corresponding reference numerals have been applied to corresponding parts.

In FIGS. 5 to 8 the top portion 8 of the funnel member 7 is the same as that of FIGS. 1 to 4, but the base portion 9 is modified. The first outlet 3 is provided in the funnel wall above the second, overflow outlet 4. The diverter device 6 comprises a membrane 30 extending across the base portion 9 between the two outlets 3, 4. In a first state the membrane 30 prevents flow to the second outlet 4, guiding it to the first outlet 3. When wetted, the membrane 30 breaks, assuming its second state in which it allows flow to the second outlet 4. Clearly, the membrane cannot return from the second state to the first state.

The first outlet 3 comprises a tube 31 extending from the base portion 9 in a direction angled slightly down from the horizontal. The receptacle 5 receives the outer end 32 of the tube 31 in a sealing manner.

The second outlet 4 is formed by the open lower end 11 of the base portion 9, and is of angled outline. It has a vertical portion 33 in line with the funnel member 7, leading to an angled end portion 34. The end portion 34 is substantially parallel to the tube 31, but is slightly longer. A projection 35 is provided on the outside of the end portion 34, adjacent to the tube 31. The external screw thread on the receptacle 5 engages with the projection 35 to attach the receptacle 5 to the device 1.

The membrane 30 is accommodated at the top of the vertical portion 33 of the overflow outlet 4, substantially in line with the lowest point 36 of the tube 31. It may be attached by adhesive or welding, and will be of any suitable sheet plastics or paper material.

As in the first embodiment, the device 1 is of any suitable plastics material, and is packaged without the receptacle 5.

For use, it is removed from the packaging and the receptacle 5 attached. The initial urine flow is guided by the membrane 30 through the first outlet 3 to the receptacle 5. The flow wets the membrane 30, which breaks, so that subsequent flow passes through the overflow outlet 4. On completion of urination the device 1 can be turned so that the receptacle 5 is closer to the vertical before it is unscrewed from the device 1. Because the sample was collected with the receptacle 5 closer to the horizontal, when it is turned there will be free space at the top of the receptacle 5 to reduce the risk of spillage. The receptacle 5 can then be re-capped and the device disposed of. As with the first embodiment, the device 1 ensures that a forestream sample is taken efficiently and cleanly, because the urine drains fully from the device 1.

In a modification it would be possible for the receptacle 5 to be attached by a push fit onto the first outlet 3 rather than by the screw thread.

What is claimed is:

1. A urine collection device for collection only of a forestream sample, comprising a collector to collect urine voided by a user, the collector comprising a top portion and a base portion, a first outlet positioned at the base portion and adapted for connection to a collection receptacle for collection of a forestream urine sample, a plug fixed in position in the first outlet adjacent the collection receptacle connected to the first outlet, a second outlet positioned in the top portion above and adjacent the first outlet, the plug having a first state allowing urine to flow through the first outlet to the receptacle for collection of the forestream sample, and upon contact with forestream urine automatically transitioning to a second state which prevents flow of further urine to the first outlet and causes all further urine to drain from the top portion after transition of the plug to the second state, the plug being unable to return from the second state to the first state, wherein the lowest part of the second outlet is substantially level with the upper end of the plug.

2. A urine collection device as claimed in claim 1, in which the second outlet is configured to prevent flow of urine to the second outlet until the second state of the plug occurs.

3. A urine collection device as claimed in claim 1, in which the plug gradually transitions into the second state upon contact with a volume of forestream urine with the plug being formed of a material which does not allow flow of urine through it the plug after expansion from contact with forestream urine.

4. A urine collection device as claimed in claim 1, in which the plug is made of a material that allows forestream urine to initially pass through the plug when in a dry state and gradually transition to the second state from contact with the forestream urine where the material prevents further urine from flowing through the plug.

5. A urine collection device as claimed in claim 1, in which the plug is of an expandable material.

6. A urine collection device as claimed in claim 1, in which the plug is configured to have an interference fit with the first outlet.

7. A urine collection device as claimed in claim 1, in which the plug is made of a material that does not drip.

8. A urine collection device as claimed in claim 1, in which the second outlet comprises a tube extending from the funnel member substantially at a right angle to the base portion and is positioned relative to the plug to cause all further urine to drain from the funnel member after transition to the second state.

9. A urine collection device as claimed in claim 8, in which the inner end of the tube is angled so that at its highest part the inner end projects into the funnel member to substantially prevent flow through the second outlet while the plug is in the first state.

10. A urine collection device as claimed in claim 8, in which the outer end of the tube is shaped to direct the flow away from the first outlet.

11. A urine collection device as claimed in claim 1, in which the plug is located relative to the first outlet in the base portion with its lower end projecting from the first outlet at its lower end and projects into the collection receptacle when the collection receptacle is attached to the device, and leaves a free space at the top of the receptacle when the collection receptacle is removed.

* * * * *